United States Patent [19]

Rule et al.

[11] Patent Number: 5,338,886
[45] Date of Patent: Aug. 16, 1994

[54] PROCESS FOR PREPARATION OF AROMATIC THIOLS

[75] Inventors: Mark Rule; James T. Tanner, III, both of Kingsport, Tenn.

[73] Assignee: Eastman Chemical Company, Kingsport, Tenn.

[21] Appl. No.: 61,468

[22] Filed: May 17, 1993

Related U.S. Application Data

[63] Continuation-in-part of Ser. No. 886,584, May 21, 1992, abandoned.

[51] Int. Cl.$^5$ ............... C07C 319/02; C07D 209/04; C07D 207/48; C07D 333/46
[52] U.S. Cl. ........................... 568/66; 568/62; 568/67; 568/68; 568/63; 560/18; 560/142; 562/432; 558/412; 548/541; 548/452; 546/290; 549/62
[58] Field of Search ............ 568/65, 66, 61, 67, 568/62, 68, 63; 560/18, 142; 562/432; 558/412; 548/541, 452; 546/290; 549/62

[56] References Cited

PUBLICATIONS

Adams & Ferriti (J. Am. Chem. Soc., 81, p. 4939, 1959).
Tiecco et al (Synthesis, 10; p. 749, 1988).
Takagi (Chem. Lett., 9, 1985; p. 1307).
Rieke et al (J. Am. Chem. Soc., 99; p. 4159, 1977).

*Primary Examiner*—Johann Richter
*Assistant Examiner*—Margaret J. Page
*Attorney, Agent, or Firm*—Charles R. Martin

[57] ABSTRACT

Disclosed is a process for preparation of an aromatic thiol corresponding to the structure A-(SH)n wherein
A is a substituted or unsubstituted aromatic radical and n is 1, 2, 3, 4, 5 or 6 comprising contacting at a temperature of at least 80° C. an aromatic halide corresponding to the structure A-Xm wherein
A is the same as above, X is bromine or iodine and n is 1, 2, 3, 4, 5, or 6
with thiourea in the presence of nickel metal.

10 Claims, No Drawings

PROCESS FOR PREPARATION OF AROMATIC THIOLS

This application is a continuation-in-part of Ser. No. 07/886,584 filed May 21, 1992 now abandoned.

This invention relates to a process of preparation of aromatic thiols wherein an aromatic halide is contacted with thiourea in the presence of nickel.

Traditional synthetic routes to aromatic thiols from aromatic halides have involved nucleophilic displacement of halogen by alkyl thiolate anions reductive cleavage of the resulting aromatic thioether with sodium metal, followed by acidification to generate the desired thiol from its sodium salt. Thus, Adams and Ferriti (J. Am. Chem. Soc., 81, 4939, 1959) disclosed a process for the preparation of aromatic dithiols and trithiols by cleavage of the corresponding ethyl thioethers with sodium metal in liquid ammonia solvent. More recently, Tiecco et al (Synthesis., 10, 749, 1988.) have disclosed the preparation of numerous aromatic thiols by cleavage of the corresponding isopropyl thioethers using sodium metal in dipolar aprotic solvents. While these processes produce good yields of the desired thiols, they involve multiple synthetic steps and would be unsuitable for large scale production of these compounds.

Recently, Takagi (Chem. Lett., 9, 1985, 1307) disclosed a process to prepare aromatic thiols which involves nucleophilic displacement of halogen by thiourea to yield the corresponding isothiuronium salt. The nucleophilic displacement of halogen by thiourea is catalyzed by a soluble nickel phosphine complex which is generated by in situ reduction of bis(triethylphosphine)nickel dichloride using sodium cyanoborohydride as the reducing agent. The desired thiol is generated by base hydrolysis of the isothiuronium salt to form the corresponding thiolate salt from which the desired thiol is generated by acidification. Although this method produces quantitative yields, there are several disadvantages to this procedure. First, a high mole ratio of catalyst to iodoaromatic (0.04:1.0) is required. Second, the active catalyst must be generated in situ requiring the use of an expensive and toxic reducing agent. Third, the catalyst cannot be recovered or regenerated from the reaction mixture. Fourth, because the reaction is catalyzed homogeneously, catalyst/product separation is difficult. Fifth, the product of the reaction is an isothiuronium salt which requires two subsequent workup steps in order to generate the desired dithiol.

Tagaki reported (Chem. Lett., 9, 1985, 1307) that deposition of nickel metal resulted in incomplete conversion of aromatic halides to the corresponding thiols. Rieke et al (J. Am. Chem. Soc., 99, 4159, 1977) reported that finely divided nickel and palladium metal powders, produced by in situ reduction of nickel and palladium salts, were unreactive toward carbon-halogen bonds. They further reported that these finely divided metals were activated towards insertion into carbon-halogen bonds only by the addition of trialkyl or triarylphosphine. Thus, the prior art teaches that the presence trialkyl or triarylphosphine is necessary for reaction of finely divided metals, in particular nickel metal, with aromatic carbon-halogen bonds.

We have now discovered a process in which aromatic halides react with thiourea in the presence of nickel to produce aromatic thiols directly instead of the isothiuronium salts.

The advantages afforded by the present invention over the prior art are numerous. First, the reaction is catalyzed heterogeneously by nickel, allowing much easier product/catalyst separation and also allows catalyst recovery. Second, the need for expensive and toxic triaryl or trialkylphosphines is eliminated. Third, in situ generation of the catalyst is unnecessary. Fourth, a much lower ratio of catalyst to aromatic halide is required. Fifth, the reaction proceeds directly to the desired thiol instead of the isothiuronium salt.

The aromatic halides which are contacted with thiourea in this invention correspond to the structure $A-X_m$ wherein A is a substituted or unsubstituted aromatic radical, X is bromine or iodine, preferably iodine, and n is 1, 2, 3, 4, 5, or 6, preferably 1, 2, 3, or 4, most preferably 2. The aromatic nucleus or moiety can contain from 6 to 18 carbon atoms, preferably 6 to 12 carbon atoms and may be carbocyclic aromatic such as benzene, biphenyl, terphenyl, naphthalene, anthracene, etc., or heterocyclic aromatic such as pyridine, thiophene, pyrrole, indole, etc. In addition to one or more halogen atoms, the aromatic moiety may be substituted by various substituents substantially inert under the conditions employed in this process. Examples of such substituents include alkyl of up to about 12 carbon atoms such as methyl, ethyl, isobutyl, hexyl, 2-ethylhexyl, nonyl, decyl, dodecyl, etc.; cycloalkyl of about 5 to 12 carbon atoms such as cyclopental, cyclohexyl, 4-butylcyclohexal, etc.; alkoxycarbonyl of from 2 to about 8 carbon atoms such as methoxycarbonyl, ethoxycarbonyl, butoxycarbonyl, hexyloxycarbonyl, etc.; carboxyl; cyano; alkenyl of about 2 to 8 carbon atoms such as vinyl allyl, etc.; formyl, alkanoyl of about 2 to 8 carbon atoms such as acetyl, propionyl, butyryl, hexanoyl, etc.; alkanoylamido of about 2 to 8 carbon atoms such as acetamido, butylamido, etc.; aroylamino such as benzamido; and alkylsulfonamide such as methanesulfonamide, hexanesulfonamide, etc. Preferably the aromatic portion of the aromatic halide is phenylene, naphthalene, biphenyl or diphenyl ether. Most preferably the aromatic portion is phenylene or naphthalene. In a particularly preferred embodiment the aromatic halide is 1,4-diiodobenzene.

The nickel catalyst useful in this reaction can be nickel metal, nickel metal on a solid support such as silica, alumina etc., or a nickel salt. Preferably, nickel metal is used. Illustrative sources of suitable nickel catalysts are commercially available nickel metal, nickel on silica/alumina, nickel on kieselguhr, raney nickel, nickel diiodide, nickel dichloride, nickel dibromide, etc. Though not bound by any particular theory, it is believed that nickel salts are reduced to nickel metal in the process provided by this invention. In general, the higher the surface area of the nickel metal, the more active it is as a catalyst for this process. The amount of nickel present is not significant as long as enough is present to catalyze the reaction. Preferably, the catalyst is present in about 0.5 to 5.0 weight percent based on the amount of aromatic halide. In general, a higher weight percent of catalyst is required for bromoaromatics than for iodoaromatics. The size of the nickel can vary widely but typically the particle size is in the range of 0.05 to 500 micrometers.

The relative amounts of aromatic halide and thiourea in this process can be varied substantially and are not critical. However, it is preferable to have at least a stoichiometric amount of thiourea relative to aromatic halide if complete conversion is desired. For polyhaloaromatics it is in general preferable to have a greater than stoichiometric amount of thiourea relative to the aromatic halide.

The process of the present invention is conducted at a temperature of at least 80° C., preferably at least 100° C. In another embodiment of the invention, the process can be conducted within a temperature range of about 80° C. to 200° C., more preferably about 100° C. to 150° C. In general, lower temperatures result in a much slower reaction rate, while higher temperatures are unnecessary.

The process of this invention is preferably carried out in a dipolar aprotic solvent such as 1-methyl-2-pyrrolidinone. Other suitable solvents include, but are not limited to, dimethylacetamide and dimethylformamide.

The aromatic thiols prepared in the process of this invention can be broadly described as corresponding to the structure A-(SH)n wherein A is the same as for the aromatic halide and n is 1, 2, 3, 4, 5 or 6, preferably 1, 2, 3, or 4 and most preferably 2.

In the process of this invention, assuming the correct stoichiometery, each of the halide atoms on the aromatic ring of the aromatic halide react with one equivalent of thiourea to place a SH group on the aromatic ring in place of the halide atom. Thus, assuming the correct stoichiometry, the number of SH groups on the aromatic ring of the aromatic thiol is the same as the number of halide atoms on the ring of the aromatic halide. For example, in the preferred embodiment wherein one equivalent of 1,4-diiodobenzene is reacted with two equivalents of thiourea the aromatic thiol would be 1,4-dithiobenzene.

The aromatic thiols prepared in accordance with this invention are useful as polymer intermediates, pesticides and herbicides.

The practice of the present invention is disclosed in the following examples, which should not be construed to limit the present invention in any way.

EXAMPLE 1

100 g (0.30 mol) 1,4-diiodobenzene, 70.0 g of thiourea (0.91 mol), and 2.0 g (2 wt. %) nickel on silica/alumina (nickel powder-surface area, 192 m²/g) were charged to a 300 mL three-neck round bottom flask equipped with a nitrogen inlet and a thermometer. 150 mL of 1-methyl-2-pyrrolidinone was added, and the reaction mixture was heated at 150° C. under nitrogen atmosphere for 8 hours. At the end of this time GLC analysis of the reaction mixture showed complete conversion of 1,4-diiodobenzene to 1,4-dithiobenzene. The hot reaction mixture was filtered through celite to remove the nickel catalyst and the hot filtrate was allowed to cool to room temperature. 500 Ml distilled water was then added in order to precipitate the product. The tan precipitate was filtered and dried under vacuum overnight. The crude 1,4-dithiobenzene precipitate (40.0 g) was purified by solvent extraction with hexane solvent. The hexane solvent was removed in vacuo to yield 24 g of 1,4-benzenedithiol, 56% yield, m.p. 98°–101° C.

EXAMPLE 2

100 g (0.26 mol) 2,6-diiodonaphthalene, 60.0 g (0.78 Mol) thiourea, and 2.0 g (2 wt. %) nickel on silica/alumina (nickel powder-surface area, 192 m²/g) were charged to a 500 mL three-neck round bottom flask equipped with mechanical stirrer, nitrogen inlet and thermometer. 350 mL 1-methyl-2-pyrrolidinone was added and the reaction mixture was heated at 150° C. with stirring under nitrogen atmosphere for 4 hours. At this time GLC analysis of the reaction mixture showed complete conversion of 2,6-diiodonaphthalene to 2,6-dithionaphthalene. The hot reaction mixture was filtered through celite in order to remove the nickel catalyst and the hot liltrate was allowed to cool to room temperature. The product was precipitated by addition of 800 mL distilled water. The grayish-white precipitate was filtered and dried under vacuum overnight. The crude dithiol (35.0 g) was purified by solvent extraction with heptane solvent. Crystallization from solvent occurred upon cooling the solution to 0° C. to yield 27.0 g of 2,6-dithionaphthalene, 60% yield, m.p. 196°–199° C.

EXAMPLE 3

100 g (0.24 mol) 4,4'diiodobiphenyl, 56.2 g (0.73 mol) thiourea, and 2.0 g (2 wt. %) nickel on silica/alumina (nickel powder-surface area, 192 m²/g) were charged to a 500 mL three-neck round bottom flask equipped with mechanical stirrer, nitrogen inlet and thermometer. 350 mL 1-methyl-2-pyrrolidinone was added and the reaction mixture was heated at 150° C. with stirring under nitrogen atmosphere for 6 hours. At this time GLC analysis of the reaction mixture showed complete conversion of 4,4'diiodobiphenyl to 4,4'-dithiobiphenyl. The hot reaction mixture was filtered through celite in order to remove the nickel catalyst and the hot filtrate was allowed to cool to room temperature. The product was precipitated by addition of 800 Ml distilled water. The tan precipitate was filtered and dried under vacuum overnight. The crude dithiol (38.0 g) was purified by solvent extraction with heptane solvent. Crystallization from solvent occurred upon cooling the solution to 0° C. to yield 26.0 g of 4,4'dithiobiphenyl, 58% yield, m.p. 177°–180° C.

EXAMPLE 4

100 g (0.42 mol) 1,4-dibromobenzene, 75.0 g (0.98 mol) thiourea, and 2,0 g (2 wt %) raney nickel were charged to a 300 mL three-neck round bottom flask equipped with a nitrogen inlet and a thermometer. 150 mL of 1-methyl-2-pyrrolidinone was added and the reaction mixture was heated at 150° C. under nitrogen atmosphere for 18 hours. At the end of this time GLC analysis of the reaction mixture showed 40% conversion to dithiol.

We claim:

1. A process for the preparation of an aromatic thiol corresponding to the structure A-(SH)n wherein A is a substituted or unsubstituted aromatic radical and n is 1, 2, 3, 4, 5 or 6 comprising contacting at a temperature in the range of 80° C. to 200° C. an aromatic halide corresponding to the structure A-Xm wherein A is the same as above, X is bromine or iodine and m is 1, 2, 3, 4, 5, or 6 with thiourea in the presence of nickel metal, wherein each of the halide atoms on the aromatic ring of the aromatic halide react with one equivalent of thiourea to place an SH group on the aromatic ring in place of the halide atom.

2. The process of claim 1 wherein A is phenylene, naphthalene, biphenyl or diphenyl ether.

3. The process of claim 1 wherein A is phenylene or napthalene.

4. The process of claim 1 wherein n is 1, 2, 3 or 4.

5. The process of claim 1 wherein X is iodine.

6. The process of claim 1 wherein m is 1, 2, 3 or 4.

7. The process of claim 1 wherein the nickel metal has a particle size in the range of 0.05 to 500 micrometers.

8. The process of claim 1 wherein the aromatic halide and thiourea are contacted with nickel in the presence of a dipolar aprotic solvent.

9. The process of claim 1 wherein the temperature is in the range of 100° C. to 150° C.

10. A process for preparation of 1,4-dithiobenzene comprising contacting 1,4-diiodobenzene with thiourea in the presence of nickel metal having a particle size in the range of 0.05 to 500 micrometers and a dipolar aprotic solvent.

* * * * *